(12) United States Patent
Yamate

(10) Patent No.: US 12,104,092 B2
(45) Date of Patent: Oct. 1, 2024

(54) ADHESIVE COMPOSITION

(71) Applicant: NIPPON SODA CO., LTD., Tokyo (JP)

(72) Inventor: Taiki Yamate, Ichihara (JP)

(73) Assignee: NIPPON SODA CO., LTD., Tokyo (JP)

( * ) Notice: Subject to any disclaimer, the term of this patent is extended or adjusted under 35 U.S.C. 154(b) by 0 days.

(21) Appl. No.: 18/244,477

(22) Filed: Sep. 11, 2023

(65) Prior Publication Data
US 2024/0002705 A1    Jan. 4, 2024

Related U.S. Application Data

(63) Continuation of application No. 16/338,869, filed as application No. PCT/JP2017/024486 on Jul. 4, 2017, now Pat. No. 11,795,353.

(30) Foreign Application Priority Data

Oct. 14, 2016 (JP) ................................. 2016-202986

(51) Int. Cl.
| | |
|---|---|
| C07C 233/07 | (2006.01) |
| C08F 22/38 | (2006.01) |
| C08F 122/38 | (2006.01) |
| C08F 222/38 | (2006.01) |
| C09D 5/00 | (2006.01) |
| C09D 133/24 | (2006.01) |
| C09D 133/26 | (2006.01) |
| C09J 133/24 | (2006.01) |
| C09J 133/26 | (2006.01) |

(52) U.S. Cl.
CPC ........... *C09J 133/26* (2013.01); *C07C 233/07* (2013.01); *C08F 22/38* (2013.01); *C08F 122/38* (2013.01); *C08F 222/38* (2013.01); *C09D 5/002* (2013.01); *C09D 133/24* (2013.01); *C09D 133/26* (2013.01); *C09J 133/24* (2013.01); *C09J 2301/30* (2020.08); *C09J 2423/006* (2013.01)

(58) Field of Classification Search
CPC ...... C08F 22/38; C08F 122/38; C08F 222/38; C07C 233/07
See application file for complete search history.

(56) References Cited

U.S. PATENT DOCUMENTS

| | | | |
|---|---|---|---|
| 2,773,063 A | 12/1956 | Specht et al. | |
| 3,402,098 A * | 9/1968 | Baum | C08F 226/02 428/435 |
| 4,126,504 A | 11/1978 | Wolinski et al. | |
| 4,155,950 A | 5/1979 | Wolinski et al. | |
| 4,308,014 A * | 12/1981 | Kawahara | A61K 6/76 526/278 |
| 4,659,784 A | 4/1987 | Chung et al. | |
| 2007/0028805 A1 | 2/2007 | Craciun et al. | |
| 2008/0187680 A1* | 8/2008 | Kawakami | B41M 5/0017 427/302 |
| 2015/0353738 A1 | 12/2015 | Yamate | |

FOREIGN PATENT DOCUMENTS

| | | |
|---|---|---|
| GB | 946107 A | 1/1964 |
| JP | S54-24026 A | 2/1979 |
| JP | H03-160459 A | 7/1991 |
| JP | 2004-217697 A | 8/2004 |
| JP | 2004-269676 A | 9/2004 |
| JP | 2013-064101 A | 4/2013 |
| MX | 2008009150 A | 1/2010 |
| TW | 201615763 A | 5/2016 |
| WO | 2014/115210 A1 | 7/2014 |

OTHER PUBLICATIONS

Aug. 15, 2017 International Search Report issued in International Patent Application No. PCT/JP2017/024486.
Apr. 16, 2019 International Preliminary Report on Patentability issued in International Patent Application No. PCT/JP2017/024486.
Zhang, Yuetao et al. "Lewis pair polymerization by classical and frustrated Lewis pairs: acid, base and monomer scope and polymerization mechanism" Dalton Transactions, vol. 41, pp. 9119-9134 (Year: 2012).

* cited by examiner

*Primary Examiner* — Ling Siu Choi
*Assistant Examiner* — David L Miller
(74) *Attorney, Agent, or Firm* — Oliff PLC

(57) ABSTRACT

An adhesive composition having excellent adhesiveness to a cycloolefin resin or the like. The adhesive composition of the present invention includes a polymer having a repeating unit derived from a polymerizable compound represented by formula (I): Y—N(Ar)(R) Formula (I), in which Ar represents an unsubstituted or substituted C6 to C14 aryl group or an unsubstituted or substituted C6 to C10 aryl C1 to C3 alkyl group; R represents an unsubstituted or substituted C1 to C6 alkyl group, an unsubstituted or substituted C3 to C6 cycloalkyl group, an unsubstituted or substituted C6 to C14 aryl group, or an unsubstituted or substituted C6 to C10 aryl C1 to C3 alkyl group; and Y represents a polymerizable functional group. In Formula (I), a substituent on Ar and a substituent on R can bond to form a divalent organic group.

1 Claim, No Drawings

ADHESIVE COMPOSITION

CROSS REFERENCE TO RELATED APPLICATIONS

This is a Continuation of application Ser. No. 16/338,869 filed Apr. 2, 2019, which in turn is a National Stage Entry of PCT/JP2017/024486 filed Jul. 4, 2017, which claims priority to JP 2016-202986 filed Oct. 14, 2016. The disclosure of the prior applications is hereby incorporated by reference herein in its entirety.

TECHNICAL FIELD

The present invention relates to a novel adhesive composition, particularly an adhesive composition having excellent adhesiveness to a plastic substrate and an adhesive composition that may be used as a coating agent or an adhesive.

This application claims priority to Japanese Patent Application No. 2016-202986, filed on Oct. 14, 2016, the contents of which are incorporated herein.

BACKGROUND ART

Patent Document 1 discloses that polymerizable compounds having a methyl group or a silyl group substituted by a plurality of aryl groups are used as coating agents having excellent adhesiveness to a cycloolefin resin.

PRIOR ART DOCUMENTS

Patent Documents

Patent Document 1: WO2014/115210

SUMMARY OF THE INVENTION

Object to be Solved by the Invention

However, the polyarylmethyl structures or the polyarylsilyl structures in these polymerizable compounds raises the production cost, and is a problem with the achievement of general-purpose functional materials. The structures thereof need to be converted into more practical structures while the adhesiveness is maintained.

Means to Solve the Object

The present inventor has studied diligently in order to achieve the above object, and as a result found that a polymer having a repeating unit derived from N,N-diphenylacrylamide exhibits adhesiveness to a cycloolefin resin. The present inventor has considered that a basic principle of the adhesiveness is CH-π interaction between an N,N-diphenyl amide group and a cycloolefin and repeats study to prepare the polymer as a more practical functional material on the basis of the principle, leading to the completion of the present invention.

That is, the present invention relates to the following inventions.

(1) An adhesive composition, comprising a polymer having a repeating unit derived from a polymerizable compound represented by formula (I):

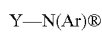 Formula (I)

(wherein Ar represents an unsubstituted or substituted C6 to C14 aryl group or an unsubstituted or substituted C6 to C10 aryl C1 to C3 alkyl group; R represents an unsubstituted or substituted C1 to C6 alkyl group, an unsubstituted or substituted C3 to C6 cycloalkyl group, an unsubstituted or substituted C6 to C14 aryl group, or an unsubstituted or substituted C6 to C10 aryl C1 to C3 alkyl group; and Y represents a polymerizable functional group, wherein a substituent on Ar and a substituent on R can bond to form a divalent organic group).

(2) The adhesive composition according to (1), wherein the polymer is a homopolymer having a repeating unit derived from one type of polymerizable compound represented by formula (I).

(3) The adhesive composition according to (1) or (2), wherein in formula (I), Y is an acryloyl group or a methacryloyl group.

(4) The adhesive composition according to any one of (1) to (3), further comprising a polymerizable compound other than the polymerizable compound represented by formula (I)

(5) The adhesive composition according to any one of (1) to (4), wherein the adhesive composition is an adhesive composition for a plastic substrate.

(6) The adhesive composition according to (5), wherein the plastic substrate is a polyolefin resin substrate.

(7) The adhesive composition according to (5), wherein the plastic substrate is a cycloolefin resin substrate.

(8) The adhesive composition according to (5), wherein the adhesive composition is a coating agent.

(9) The adhesive composition according to (8), wherein the coating agent is a primer.

(10) The adhesive composition according to (5), wherein the adhesive composition is an adhesive.

Effect of the Invention

By using the adhesive composition of the present invention, a coating film having excellent adhesiveness to a plastic substrate, particularly a substrate of a plastic such as a cycloolefin resin may be formed. A functional film that may not be conventionally directly formed on a plastic substrate may be laminated via the coating film of the present invention. Further, plastic substrates may be adhered together via a coating film.

Since the surface does not need to be modified by UV-ozone treatment, the initial characteristics of the plastic substrate may be maintained.

It may also be used as an adhesive.

MODE OF CARRYING OUT THE INVENTION

1. Adhesive Composition

[Polymer]

The adhesive composition of the present invention comprises a polymer having a repeating unit derived from a polymerizable compound represented by formula (I) (occasionally called "polymer (I)").

In the formula, Ar represents an unsubstituted or substituted C6 to C14 aryl group or an unsubstituted or substituted C6 to C10 aryl C1 to C3 alkyl group.

As the C6 to C14 aryl group, specifically, a phenyl group, a naphthyl group, an anthracenyl group, a phenanthrenyl group, or the like is exemplified.

As the C6 to C10 aryl C1 to C3 alkyl group, a benzyl group, a phenethyl group, a naphthalen-1-ylmethyl group, or the like is exemplified.

As the "substituent" in "unsubstituted or substituted", specifically, a halogeno group, a hydroxy group, a C1 to C6 alkyl group, a C1 to C6 alkoxy group, a C3 to C6 cycloalkyl group, a C6 to C10 aryl group, a benzyl group, an α,α-dimethylbenzyl group, a mercapto group, a C1 to C6 alkylthio group, an amino group, a C1 to C6 alkylamino group, a C1 to C6 dialkylamino group, a nitro group, or a cyano group is exemplified. As long as the number of substituents may be chemically permitted, it is not limited.

As the halogeno group, specifically, a fluoro group, a chloro group, a bromo group, and an iodo group are exemplified.

As the C1 to C6 alkyl group, specifically, a methyl group, an ethyl group, a n-propyl group, an i-propyl group, a n-butyl group, a s-butyl group, an i-butyl group, a t-butyl group, a n-pentyl group, a n-hexyl group, or the like is exemplified.

As the C1 to C6 alkoxy group, specifically, a methoxy group, an ethoxy group, a n-propoxy group, an i-propoxy group, a n-butoxy group, a s-butoxy group, an i-butoxy group, a t-butoxy group, a n-pentoxy group, a n-hexoxy group, or the like is exemplified.

As the C3 to C6 cycloalkyl group, specifically, a cyclopropyl group, a cyclobutyl group, a cyclopentyl group, a cyclohexyl group, or the like is exemplified.

As the C6 to C10 aryl group, specifically, a phenyl group, a naphthyl group, or the like is exemplified.

As the C1 to C6 alkylthio group, specifically, a methylthio group, an ethylthio group, a n-propylthio group, an i-propylthio group, a n-butylthio group, a s-butylthio group, an i-butylthio group, a t-butylthio group, a n-pentylthio group, a n-hexylthio group, or the like is exemplified.

As the C1 to C6 alkylamino group, specifically, a methylamino group, an ethylamino group, a n-propylamino group, an i-propylamino group, a n-butylamino group, an i-butylamino group, a t-butylamino group, a n-pentylamino group, a n-hexylamino group, or the like is exemplified.

As the C1 to C6 dialkylamino group, specifically, an N,N-dimethylamino group, an N,N-diethylamino group, an ethyl(methyl)amino group, or the like is exemplified.

In the present invention, as Ar, an unsubstituted or substituted C6 to C10 aryl group is preferred. As the substituent, a C1 to C6 alkyl group and a C1 to C6 alkoxy group are preferred.

In the formula, R represents an unsubstituted or substituted C1 to C6 alkyl group, an unsubstituted or substituted C3 to C6 cycloalkyl group, an unsubstituted or substituted C6 to C14 aryl group, or an unsubstituted or substituted C6 to C10 aryl C1 to C3 alkyl group.

As specific examples of the C1 to C6 alkyl group, the C3 to C6 cycloalkyl group, the C6 to C14 aryl group, the C6 to C10 aryl C1 to C3 alkyl group and the substituent thereof, the same as those exemplified in the above Ar is mentioned. In the present invention, as R, an unsubstituted or substituted C6 to C10 aryl group is preferred. As the substituent, a C1 to C6 alkyl group and a C1 to C6 alkoxy group are preferred.

In the present invention, the substituent on Ar and the substituent on R may bond to form a divalent organic group.

As the divalent organic group, specifically, a methylene group, a dimethylene group, an oxo group, a sulfenyl group, a carbonyl group, an imino group, or a C1 to C6 alkyl imino group may be exemplified.

In the formula, Y represents a polymerizable functional group. As the polymerizable functional group, a group or the like such as an acryloyl group, a methacryloyl group, a vinyloxycarbonyl group, a prop-1-en-2-yloxycarbonyl group or an allyloxycarbonyl group having a polymerizable carbon-carbon double bond is exemplified.

In the present invention, as Y, an acryloyl group and a methacryloyl group are preferred.

Among polymerizable compounds used for the present invention and represented by formula (I), N,N-diphenylacrylamide or N,N-diphenylmethacrylamide is exemplified preferably.

The polymer used in the present invention may be used without particular limitation as long as it is a polymer obtained by polymerizing the polymerizable compound represented by formula (I). The polymerization reaction is not particularly limited, and may be a known method for synthesizing a polyacrylate, or the like, and, for example, radical polymerization, anionic polymerization, or the like may be exemplified.

The molecular weight of the polymer used is not limited as long as it is in a range in which application onto a substrate is possible. For example, a polymer having a number average molecular weight in the range of 1,000 to 300,000, 5,000 to 200,000, 10,000 to 100,000, or the like may be exemplified.

The molecular weight distribution (PDI) of the polymer according to the present invention is the ratio of the weight average molecular weight/the number average molecular weight (Mw/Mn), preferably 1.0 to 5.0, more preferably 1.0 to 4.0, and most preferably 1.0 to 3.0.

The weight average molecular weight and the number average molecular weight are values obtained by converting data measured by gel permeation chromatography (GPC) using DMF as a solvent based on the molecular weight of poly(methylmethacrylate) used as a standard.

The polymer used for the present invention may be a polymer having the repeating unit derived from the polymerizable compound represented by formula (I), and may be a copolymer having a repeating unit derived from a polymerizable compound other than the polymerizable compound represented by formula (I) such as a repeating unit derived from a (meth)acrylate monomer, a repeating unit derived from an aromatic vinyl monomer, a repeating unit derived from an olefin monomer.

Particularly it is preferred that it is a homopolymer obtained by polymerizing one polymerizable compound represented by formula (I), or a polymer obtained by polymerizing two or more polymerizable compounds represented by formula (I).

As the polymerizable compound other than the polymerizable compound represented by formula (I), specifically, a (meth)acrylate such as methyl (meth)acrylate, ethyl (meth)acrylate, n-propyl (meth)acrylate, butyl (meth)acrylate, i-butyl (meth)acrylate, n-hexyl (meth)acrylate, 2-ethylhexyl (meth)acrylate, decyl (meth)acrylate, lauryl (meth)acrylate, stearyl (meth)acrylate, cyclohexyl (meth)acrylate, or trityl (meth)acrylate;

a vinyl compound such as styrene, vinyl acetate, vinyl chloride, vinylidene chloride, acrylonitrile, vinyl ether, acrolein, or divinylbenzene; or an olefin compound such as ethylene, propylene, or butadiene is exemplified.

[Other Components]
(Organic Solvent)

An organic solvent may be comprised in the adhesive composition of the present invention. As a typical organic solvent that may be used, an ether-based organic solvent, an ester-based organic solvent, an aliphatic hydrocarbon-based organic solvent, an aromatic hydrocarbon-based organic solvent, a ketone-based organic solvent, an organohalide-based organic solvent, or the like is exemplified.

As the ether-based organic solvent, diethyl ether, dipropyl ether, dibutyl ether, diamyl ether, or the like is exemplified; as the ester-based organic solvent, ethyl acetate, propyl acetate, butyl acetate, amyl acetate, heptyl acetate, ethyl butyrate, isoamyl isovalerate, or the like is exemplified; as the aliphatic hydrocarbon-based organic solvent, normal hexane, normal heptane, cyclohexane, or the like is exemplified; as the aromatic hydrocarbon-based organic solvent, toluene, xylene, or the like is exemplified; as the ketone-based organic solvent, methyl ethyl ketone, methyl isobutyl ketone, cyclohexanone, or the like is exemplified; and as the organohalide-based organic solvent, trichloroethane, trichloroethylene, or the like is exemplified. Further, a relatively inactive organic solvent such as propylene glycol monomethyl ether or propylene glycol monoethyl ether may also be used.

Especially, an ester-based organic solvent such as propyl acetate, butyl acetate, isoamyl acetate, heptyl acetate, ethyl butyrate, or isoamyl isovalerate having volatility is preferred considering that the present invention is often used in an open system in a natural environment.

(Polymerizable Compound)

The adhesive composition of the present invention may comprise a polymerizable compound other than the polymerizable compound represented by formula (I).

The polymerizable compound may be properly selected depending on target physical properties such as the melting point, viscosity, and the refractive index, and is not particularly limited, but specifically the following are exemplified:

A monofunctional (meth)acrylate such as methyl (meth)acrylate, ethyl (meth)acrylate, n-propyl (meth)acrylate, butyl (meth)acrylate, i-butyl (meth)acrylate, n-hexyl (meth)acrylate, 2-ethylhexyl (meth)acrylate, decyl (meth)acrylate, lauryl (meth)acrylate, stearyl (meth)acrylate, cyclohexyl (meth)acrylate, or trityl (meth)acrylate;

- a bifunctional (meth)acrylate such as ethylene glycol di(meth)acrylate, diethylene glycol di(meth)acrylate, triethylene glycol di(meth)acrylate, polyethylene glycol di(meth)acrylate, propylene glycol di(meth)acrylate, dipropylene glycol di(meth)acrylate, polypropylene glycol di(meth)acrylate, propanediol di(meth)acrylate, glycerin di(meth)acrylate, cyclohexanediol di(meth)acrylate, bis[(meth)acryloxymethyl]cyclohexane, bisphenol A-di(meth)acrylate, or a di(meth)acrylate of an alkylene oxide adduct of bisphenol A; or
- a polyfunctional, trifunctional or higher, (meth)acrylate such as trimethylolpropane tri(meth)acrylate, pentaerythritol tetra(meth)acrylate, dipentaerythritol penta(meth)acrylate, or dipentaerythritol hexa(meth)acrylate.

An acrylic polymerizable oligomer such as epoxy (meth)acrylate, urethane (meth)acrylate, a polyester (meth)acrylate, a (meth)acrylate of a polybutadiene oligomer, a polyamide (meth)acrylic oligomer, melamine (meth)acrylate, a (meth)acrylate of a cyclopentadiene oligomer, a (meth)acrylate of a silicone oligomer.

A vinyl compound such as styrene, vinyl acetate, vinyl chloride, vinylidene chloride, acrylonitrile, vinyl ether, acrolein, or divinylbenzene; or an olefin compound such as ethylene, propylene, or butadiene.

As long as the adhesiveness of the adhesive composition is not deteriorated, the added amount of the polymerizable compound is not limited. The blended amount of the polymerizable compound is preferably less than 50% by mass, and more preferably less than 30% by mass with respect to the polymer (I).

(Polymerization Initiator)

The adhesive composition of the present invention may comprise a polymerization initiator. Here, as the polymerization reaction, a photopolymerization reaction, a thermal polymerization reaction, or the like is exemplified, and the photopolymerization reaction, which has no thermal influence on a plastic substrate, is preferred. As the light used in the photopolymerization reaction, ultraviolet rays or visible light is exemplified, and ultraviolet rays, which cause a high polymerization rate, are preferred.

As the photopolymerization initiator, (a) a compound that generates a cationic species by light irradiation, and (b) a compound that generates an active radical species by light irradiation, or the like may be exemplified.

As the compound that generates a cationic species by light irradiation, for example, an onium salt in which the cationic moiety is a sulfonium, iodonium, diazonium, ammonium, or (2,4-cyclopentadien-1-yl) [(1-methylethyl)benzene]-Fe cation, and the anionic moiety is composed of $BF_4—$, $PF_5—$, $SbF_6—$, or $[BX_4]—$ (X represents a phenyl group substituted by at least two or more fluorine atoms or a trifluoromethyl group) is exemplified.

Specifically, as the sulfonium salt, bis[4-(diphenylsulfonio)phenyl]sulfide bishexafluorophosphate, bis[4-(diphenylsulfonio)phenyl]sulfide bishexafluoroantimonate, bis[4-(diphenylsulfonio)phenyl]sulfide bistetrafluoroborate, bis[4-(diphenylsulfonio)phenyl]sulfide tetrakis(pentafluorophenyl)borate, diphenyl-4-(phenylthio)phenylsulfonium hexafluorophosphate, diphenyl-4-(phenylthio)phenylsulfonium hexafluoroantimonate, diphenyl-4-(phenylthio)phenylsulfonium tetrafluoroborate, diphenyl-4-(phenylthio)phenylsulfonium tetrakis(pentafluorophenyl)borate, triphenylsulfonium hexafluorophosphate, or the like is exemplified.

As the iodonium salt, diphenyliodonium hexafluorophosphate, diphenyliodonium hexafluoroantimonate, diphenyliodonium tetrafluoroborate, diphenyliodonium tetrakis(pentafluorophenyl)borate, bis(dodecylphenyl)iodonium hexafluorophosphate, bis(dodecylphenyl)iodonium hexafluoroantimonate, bis(dodecylphenyl)iodonium tetrafluoroborate, bis(dodecylphenyl)iodonium tetrakis(pentafluorophenyl)borate, or the like is exemplified.

As the diazonium salt, phenyldiazonium hexafluorophosphate, phenyldiazonium hexafluoroantimonate, phenyldiazonium tetrafluoroborate, phenyldiazonium tetrakis(pentafluorophenyl)borate, or the like is exemplified.

As the ammonium salt, 1-benzyl-2-cyanopyridinium hexafluorophosphate, 1-benzyl-2-cyanopyridinium hexafluoroantimonate, 1-benzyl-2-cyanopyridinium tetrafluoroborate, 1-benzyl-2-cyanopyridinium tetrakis(pentafluorophenyl)borate, 1-(naphthylmethyl)-2-cyanopyridinium hexafluorophosphate, 1-(naphthylmethyl)-2-cyanopyridinium hexafluoroantimonate, 1-(naphthylmethyl)-2-cyanopyridinium tetrafluoroborate, 1-(naphthylmethyl)-2-cyanopyridinium tetrakis(pentafluorophenyl)borate, or the like is exemplified.

As the (2,4-cyclopentadien-1-yl)[(1-methylethyl)benzene]-Fe salt, (2,4-cyclopentadien-1-yl) [(1-methylethyl)benzene]-Fe(II) hexafluorophosphate, (2,4-cyclopentadien-1-yl) [(1-methylethyl)benzene]-Fe(II) hexafluoroantimonate, (2,4-cyclopentadien-1-yl) [(1-methylethyl)benzene]-Fe(II) tetrafluoroborate, (2,4-cyclopentadien-1-yl) [(1-methylethyl)benzene]-Fe(II) tetrakis(pentafluorophenyl)borate, or the like is exemplified.

As the compound that generates an active radical species by light irradiation, specifically, acetophenone, acetophenone benzyl ketal, 1-hydroxycyclohexyl phenyl ketone, 2,2-dimethoxy-1,2-diphenylethan-1-one, xanthone, fluorenone, benzaldehyde, fluorene, anthraquinone, triphenylamine, carbazole, 3-methylacetophenone, 4-chlorobenzophenone, 4,4'-dimethoxybenzophenone, 4,4'-diaminobenzophenone, benzoin propyl ether, benzoin ethyl ether, benzyl dimethyl ketal, 1-(4-isopropylphenyl)-2-hydroxy-2-methylpropan-1-one, 2-hydroxy-2-methyl-1-phenylpropan-1-one, thioxanthone, diethylthioxanthone, 2-isopropylthioxanthone, 2-chlorothioxanthone, 2-methyl-1-[4-(methylthio)phenyl]-2-morpholino-propan-1-one, 2-benzyl-2-dimethylamino-1-(4-morpholinophenyl)-butanone-1,4-(2-hydroxyethoxy) phenyl-(2-hydroxy-2-propyl) ketone, 2,4,6-trimethylbenzoyldiphenylphosphine oxide, bis-(2,6-dimethoxybenzoyl)-2,4,4-trimethylpentylphosphine oxide, oligo(2-hydroxy-2-methyl-1-(4-(1-methylvinyl)phenyl)propanone), or the like is exemplified.

The thermal polymerization initiator refers to a compound that generates a radical by heating, and an organic peroxide, an azo compound, and a redox initiator, or the like is exemplified.

For the blended amount of the polymerization initiator used in the present invention, 0.01 to 20% by mass of the polymerization initiator is preferably blended, and 0.1 to 10% by mass is further preferred with respect to the total amount of all polymerizable compounds.

[Provision of Functionality]
(Condensate of Organosilane Compound)

A condensate of an organosilane compound may be comprised in the adhesive composition of the present invention for the purpose of inorganizing the surface of a coating film. Thus, a glassy hard coat layer may be laminated on the surface of a plastic substrate.

The condensate of the organosilane compound may be produced from an organosilane compound represented by formula (A) using a known silanol condensation method.

$$R^4Si(R^3)_3 \tag{A}$$

wherein $R^4$ represents a C1 to C30 alkyl group, a C2 to C8 alkenyl group, or a C6 to C10 aryl group optionally substituted by an epoxy group, a glycidyloxy group, or a (meth)acryloxy group; and $R^3$ represents a hydroxy group or a hydrolyzable group.

As the C1 to C30 alkyl group for $R^4$, a methyl group, an ethyl group, a n-propyl group, an isopropyl group, a n-butyl group, an isobutyl group, a s-butyl group, a t-butyl group, a n-pentyl group, an isopentyl group, a neopentyl group, a 2-methylbutyl group, a 2,2-dimethylpropyl group, a n-hexyl group, an isohexyl group, a n-heptyl group, a n-octyl group, a nonyl group, an isononyl group, a decyl group, a lauryl group, a tridecyl group, a myristyl group, a pentadecyl group, a palmityl group, a heptadecyl group, a stearyl group, or the like is exemplified. As the C2 to C8 alkenyl group, a vinyl group, an allyl group, a 2-propenyl group, or the like is exemplified.

As the C6 to C10 aryl group, a phenyl group, a naphthyl group, or the like is exemplified.

The hydrolyzable group of $R^3$ means a group that may be hydrolyzed by heating at 25° C. to 100° C. under catalyst-free conditions or in the coexistence of excess water to produce a silanol group, or a group that may form a siloxane condensate. Specifically, an alkoxy group, an acyloxy group, a halogeno group, an isocyanate group, or the like may be exemplified, and a C1 to C4 alkoxy group or a C1 to C6 acyloxy group is preferred.

Here, as the C1 to C4 alkoxy group, a methoxy group, an ethoxy group, a n-propoxy group, an isopropoxy group, a n-butoxy group, an isobutoxy group, a t-butoxy group, or the like is exemplified, the C1 to C6 acyloxy group means an acyloxy group having 1 to 6 carbon atoms besides a carbonyl group, and as the C1 to C6 acyloxy group, an acetyloxy group, a benzoyloxy group, or the like is exemplified. As the halogeno group, a fluoro group, a chloro group, a bromo group, an iodo group, or the like is exemplified.

As the organosilane compound represented by formula (A), specifically, vinyltrichlorosilane, vinyltrimethoxysilane, vinyltriethoxysilane, vinyltributoxysilane, vinyltriisopropoxysilane, allyltrimethoxysilane, 3-butenyltrimethoxysilane, divinyldichlorosilane, divinyldiacetoxysilane, divinyldimethoxysilane, diallyldimethoxysilane, di-3-butenyldimethoxysilane, vinylmethyldimethoxysilane, vinylethyldiethoxysilane, methyltri(meth)acryloxysilane, methyltris[2-(meth)acryloxyethoxy]silane, methyltriglycidyloxysilane, methyltris(3-methyl-3-oxetanemethoxy)silane, methyltrichlorosilane, methyltrimethoxysilane, methyltriethoxysilane, methyltributoxysilane, ethyltrimethoxysilane, ethyltriisopropoxysilane, ethyltri(n-butoxy)silane, n-butyltrimethoxysilane, dimethyldichlorosilane, dimethyldiacetoxysilane, dimethyldimethoxysilane, di-n-butyldimethoxysilane, 2-cyclopropenyltrimethoxysilane, 2-cyclopentenyltrimethoxysilane, trifluoromethyltrimethoxysilane, phenyltrimethoxysilane, diphenyldimethoxysilane, pentafluorophenyltrimethoxysilane, 4-oxacyclohexyltrimethoxysilane, 2-(3,4-epoxycyclohexyl)ethyltrimethoxysilane, 3-glycidyloxy-n-propylmethyldiethoxysilane, 3-glycidyloxy-n-propyltrimethoxysilane, 3-glycidyloxy-n-propyltriethoxysilane, 3-methacryloxy-n-propylmethyldimethoxysilane, 3-methacryloxy-n-propyltrimethoxysilane, 3-methacryloxy-n-propylmethyldiethoxysilane, 3-methacryloxy-n-propyltriethoxysilane, 3-acryloxy-n-propyltrimethoxysilane, or the like is exemplified.

As the known silanol condensation method, specifically a method using a silanol condensation catalyst may be exemplified. The silanol condensation catalyst is not particularly limited as long as the hydrolyzable group in the compound represented by formula (A) is hydrolyzed, and the silanol is condensed to form a siloxane bond. An organic metal, an organic acid metal salt, a metal hydroxide, an acid, a base, a metal complex, a hydrolysate thereof, a condensate thereof, or the like is exemplified. The silanol condensation catalyst may be used alone or used by combination of two or more thereof.

As the organic metal, specifically, an alkyl metal compound such as tetramethyltitanium or tetrapropylzirconium; a metal alcoholate such as Titanium(IV)tetraisopropoxide or zirconium(IV)tetrabutoxide; or the like is exemplified.

The organic acid metal salt is a compound consisting of a salt obtained from a metal ion and an organic acid, and as the organic acid, an organic compound that exhibits acidity, such as a carboxylic acid such as acetic acid, oxalic acid, tartaric acid, or benzoic acid; a sulfur-containing organic acid such as sulfonic acid or sulfinic acid; a phenol compound; an enol compound; an oxime compound; an imide compound; or an aromatic sulfonamide is exemplified. Specifically, a metal carboxylate, a metal sulfonate, a phenol metal salt, or the like is exemplified.

The metal hydroxide is a metal compound having a hydroxide ion as an anion.

The metal complex is preferably a metal complex having a hydroxy group or a hydrolyzable group, and more preferably a metal complex having two or more hydroxy groups or hydrolyzable groups. Having two or more hydroxy groups or hydrolyzable groups means that the total of hydrolyzable groups and hydroxyl groups is two or more.

As the hydrolyzable group, an alkoxy group, an acyloxy group, a halogen group, and an isocyanate group are exemplified, and a C1 to C4 alkoxy group and a C1 to C4 acyloxy group are preferred.

As the above metal complex, a β-ketocarbonyl compound, a β-ketoester compound, and an α-hydroxyester compound are preferred, and specifically a compound in which a β-ketoester such as methyl acetoacetate, n-propyl acetoacetate, isopropyl acetoacetate, n-butyl acetoacetate, sec-butyl acetoacetate, or t-butyl acetoacetate; a β-diketone such as acetylacetone, hexane-2,4-dione, heptane-2,4-dione, heptane-3,5-dione, octane-2,4-dione, nonane-2,4-dione, or 5-methyl-hexane-2,4-dione; a hydroxycarboxylic acid such as glycolic acid or lactic acid; or the like is coordinated in the metal element is exemplified.

As the metal element in these organic metal, organic acid metal salt, metal hydroxide, and metal complex, titanium (Ti), zirconium (Zr), aluminum (Al), silicon (Si), germanium (Ge), indium (In), tin (Sn), tantalum (Ta), zinc (Zn), tungsten (W), lead (Pb), or the like is exemplified, and among these, titanium (Ti), zirconium (Zr), aluminum (Al), and tin (Sn) are preferred, and particularly titanium (Ti) is preferred. These metals may be used alone or may be used by combination of two or more thereof.

As the acid, an organic acid and a mineral acid are exemplified. As the organic acid, acetic acid, formic acid, oxalic acid, phthalic acid, trifluoroacetic acid, p-toluenesulfonic acid, methanesulfonic acid, or the like is exemplified, and as the mineral acid, hydrochloric acid, nitric acid, carbonic acid, boric acid, hydrofluoboric acid, or the like is exemplified.

Here, a photo-acid-generating agent that generates an acid by light irradiation, specifically, diphenyliodonium hexafluorophosphate, triphenylphosphonium hexafluorophosphate, and the like, is also included in the acid.

As the base, a strong base such as tetramethylguanidine or tetramethylguanidylpropyltrimethoxysilane; an organic amine, a carboxylic acid-neutralized salt of an organic amine, a quaternary ammonium salt, or the like is exemplified.

The blending ratio of the silanol condensation catalyst is 1:99 to 99:1, and preferably 1:99 to 50:50, with respect to the mass of the organosilane compound.

(Metal Compound and the Like)

A metal compound may be added to the adhesive composition of the present invention for the purpose of increasing the refractive index and hardness of the coating film. As the metal compound, the above-described organosilane compound, and the organic metal, the organic acid metal salt, the metal hydroxide, and the metal complex exemplified as the silanol condensation catalyst are exemplified. As a metal compound other than these, a metal oxide is exemplified, and specifically, particles of a metal oxide that is silicon dioxide, titanium oxide, aluminum oxide, chromium oxide, manganese oxide, iron oxide, zirconium oxide (zirconia), or cobalt oxide, or the like are exemplified. Particularly zirconium oxide is preferred.

As the shape of the particles, a spherical form, a porous powder form, a scaly form, a fibrous form, or the like is exemplified, and the shape of the particles is more preferably a porous powder form.

As the metal oxide particles of the present invention, colloidal metal oxide particles may also be used. Specifically, colloidal silica and colloidal zirconium may be exemplified, and water-dispersed colloidal metal oxide particles or colloidal metal oxide particles dispersed in an organic solvent such as methanol or isopropanol may be exemplified.

For the coloration of the coating film, film thickening, the prevention of the transmission of ultraviolet rays, the provision of anticorrosiveness, and the development of properties such as heat resistance, a filler may also be separately added and dispersed. As the filler, a water-insoluble pigment such as an organic pigment or an inorganic pigment, a particulate, fibrous, or scaly metal and alloy and oxide, hydroxide, carbide, nitride, and sulfide thereof other than a pigment, or the like are exemplified.

In addition, additives such as a known dehydrating agent such as methyl orthoformate, methyl orthoacetate, or tetraethoxysilane, various surfactants, and a silane coupling agent other than the above, a titanium coupling agent, a dye, a dispersing agent, a thickening agent, and a leveling agent may also be added.

In the present invention, additive components such as a sensitizer, an ultraviolet absorbing agent, a dye, a rust preventive, and a preservative may be blended as required.

[Preparation of Adhesive Composition]

The adhesive composition in the present invention is usually prepared by mixing, in addition to the polymer (I), the above polymerizable compound, the above condensate of the organosilane compound, a photopolymerization initiator, a metal compound, and the like as required, in an organic solvent. The solid content of the adhesive composition of the present invention is preferably 1 to 90, by mass, and more preferably 5 to 60% by mass.

2. Formed Body

The formed body of the present invention is a formed body in which a film (coating film) obtained by applying the above adhesive composition to a plastic substrate, and curing the above adhesive composition is provided directly on the substrate.

[Substrate]

As the substrate on which the adhesive composition of the present invention may be used, a plastic substrate is preferred, and, specifically, a cycloolefin resin such as a cycloolefin polymer or a cycloolefin copolymer; a polyolefin resin such as polyethylene, polypropylene, polyisoprene, polybutadiene, polymethylpentene; a polycarbonate resin; a polyisocyanate resin; a polyimide resin; a polyester resin; an acrylic resin; a methacrylic resin; an epoxy resin; a polyethylene terephthalate resin; or an aromatic polyether ketone resin is exemplified.

Particularly a cycloolefin resin and a polyolefin resin are preferably used.

[Formation of Coating Film]

The polymer (I) in the adhesive composition of the present invention firmly adheres via CH-π interaction to the surface of a substrate. Therefore, a coating film may be formed if only the adhesive composition is heat-dried after application. When the adhesive composition further comprises a polymerizable compound, ultraviolet irradiation treatment using the photopolymerization initiator in combination or heat treatment using the thermal polymerization initiator in combination is preferably performed.

Since the surface of the substrate does not need to be modified by UV-ozone treatment or the like, the initial characteristics of the plastic substrate may be maintained.

As the method for applying the adhesive composition, a known application method may be used, and a dipping method, a spraying method, a bar coating method, a roll coating method, a spin coating method, a curtain coating method, a gravure printing method, a silk screen method, an ink jet method, or the like is exemplified. The thickness of the formed coating film is not particularly limited, and is about 0.1 to 200 μm.

The heating and drying treatment of the coating film is preferably performed at 40 to 200° C. for about 0.5 to 120 minutes, and more preferably at 60 to 120° C. for about 1 to 60 minutes.

The irradiation with ultraviolet rays may be performed using a known apparatus such as a high pressure mercury lamp, a low pressure mercury lamp, a metal halide lamp, or an excimer lamp.

Heat treatment may be performed sequentially with drying treatment.

[Lamination of Functional Film]

Since the coating film of the present invention has very good adhesiveness to a plastic substrate, the coating film of the present invention may be used as a primer layer. Therefore, a functional film that may not be conventionally formed directly on a plastic substrate may be laminated via the coating film of the present invention. A plurality of layers may be laminated, and also a layer or layers may further be laminated by further applying the coating agent of the present invention to the plurality of layers.

As the functional film, a conductive film, an antireflection film, a gas barrier film, a hard coat film, a water-repellent film, a hydrophilic film, or the like is exemplified.

As the conductive film, a film of indium oxide doped with tin (ITO film), a film of tin oxide doped with fluorine (FTO film), a film of zinc oxide doped with antimony, a film of zinc oxide doped with indium, or the like is exemplified.

The gas barrier film is not particularly limited as long as it has gas barrier properties against oxygen, water vapor, and the like, and the gas barrier film is preferably a thin film of an inorganic compound, and particularly a thin film of a metal oxide, a metal nitride, or a metal carbide having a metal element selected from the group consisting of titanium, zirconium, aluminum, silicon, germanium, indium, tin, tantalum, zinc, tungsten, and lead, or a composite thereof is preferred.

The thickness of these functional films is usually 10 to 300 nm, preferably 10 to 200 nm, and more preferably 10 to 100 nm.

For the method for forming a conductive film, a gas barrier film, or the like, consisting of an inorganic compound on the coating film of the present invention, the transparent conductive film or the gas barrier film may be formed by a known method, and the formation may be performed by a physical method such as a sputtering method, a vacuum deposition method, or an ion plating method, a chemical method such as a spraying method, a dipping method, a thermal CVD method, or a plasma CVD method, or the like.

For example, according to a sputtering method or the like, a film consisting of silicon oxide may also be formed by using as a target a sintered body obtained by sintering a silicon compound in the presence of oxygen gas, or the like, or a film may also be formed by reactively sputtering metal silicon as a target in the presence of oxygen. According to a plasma CVD method, a film consisting of silicon oxynitride on a substrate may be formed by supplying silane gas together with oxygen gas and nitrogen gas into a chamber in which a plasma is generated, to react them. According to a thermal CVD method or the like, a film consisting of silicon oxide may be formed by using as an evaporant an organic solvent solution containing a silicon compound, or the like.

In the present invention, the functional film is preferably formed particularly by a sputtering method, a vacuum deposition method, an ion plating method, or a plasma CVD method. When the functional film is formed, the surface of the coating film of the present invention may be previously plasma-treated or UV-ozone-treated as required.

The coating film of the present invention may also be used as an adhesive layer used when plastic substrates, or a plastic substrate and another formed sheet are adhered.

As the formed sheet, a plastic sheet consisting of a material such as a polyvinyl chloride resin, a cellulose resin, a polyethylene resin, a polystyrene resin, an ABS resin, a polyamide resin, a polyester resin, a polyurethane resin, or a cycloolefin resin; an optical film such as a polarizing plate, a phase difference film, or an antireflection film; metallic foil such as aluminum, copper, or silicon; or the like may be exemplified.

Examples will be shown below, but the technical scope of the present invention is not limited by these Examples.

EXAMPLES

The measurement of the number average molecular weights of polymers obtained in Examples was performed with the following device under the following conditions.

[Device]
Sample injector: Waters 2695 Alliance
Separation column: Shodex SB-G, SB-806HQ, SB-805HQ, SB-804HQ, SB-803HQ
Detector: Waters 2414 refractive index (RI) detector 2998 Photodiode array (PDA) detector
Column oven: column oven manufactured by Waters Corporation

[Conditions]
Column oven temperature: 40° C.
RI detector temperature: 40° C.
Mobile phase: DMF
Flow rate: 1.0 mL/min
Standard injection rate: 200 μL
PDA detector extraction wave: 254.0 nm
Quantitative calculation: in terms of a standard poly (methyl methacrylate) equivalent average molecular weight Example 1

(1) Synthesis of N,N-Diphenylacrylamide

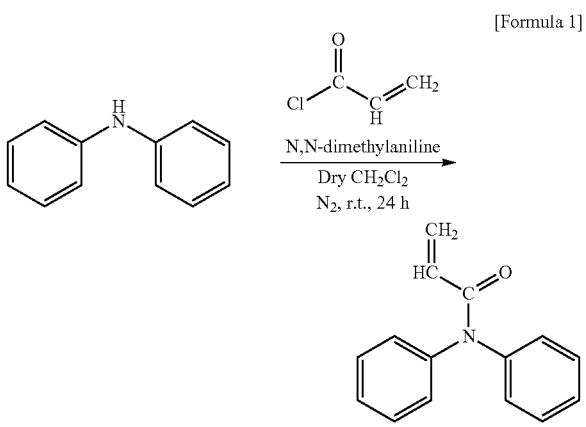

[Formula 1]

Diphenylamine (5.00 g, 29.6 mmol), N,N-dimethylaniline (5.37 g, 44.3 mmol), and 50 mL of super-dehydrated dichloromethane were added to a 100 mL four-necked flask replaced with nitrogen. The reaction solution was cooled to 10° C. or less in an ice bath, acrylic acid chloride (3.21 g, 35.5 mmol) was slowly dropped, and the mixture was stirred for 30 minutes. Then, the temperature of the reaction mixture was raised to room temperature, and the reaction was performed for 24 hours. After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The crude product was recrystallized with toluene/hexane to obtain N,N-diphenylacrylamide (4.61 g, yield 70%).

The result of mass spectrometry analysis is shown below.
High Resolution ESI-TOF-MS m/z Calcd. for $[C_{15}H_{13}N_1O_1([M+Na]^+)]$: 246.0889 found 246.0880.

(2) Preparation of Poly(N,N-Diphenylacrylamide)

The polymer was prepared by a radical polymerization reaction using azobisisobutyronitrile (AIBN) as an initiator.

To a 50 mL Schlenk tube were added 1.00 g of N,N-diphenylacrylamide and 7.35 mg of AIBN. A stirring bar was placed, and the Schlenk tube was sealed with a three-way cock, and then a gas sampling bag containing nitrogen was placed. The container was degassed by a vacuum pump, and then replaced with nitrogen. Then, 4.00 mL of deoxygenated toluene was added, and the mixture was heated in an oil bath at 65° C. for 24 hours, resulting in a radical polymerization reaction. After the completion of the reaction, the reaction liquid was added to methanol for reprecipitation. By GPC, the number average molecular weight ($M_n$) of the polymer was 23,100, and the molecular weight distribution (PDI) was 1.39.

(3) Preparation of Coating Agent

Then, 0.1 g of poly(N,N-diphenylacrylamide) was dissolved in 9.9 g of cyclohexanone by heating to obtain a coating agent (A-1) having a solid concentration of 1 wt %.

(4) Formation of Coating Film

Films composed of the coating agent (A-1) were formed on various substrates of a size of 50×50 mm by bar coating. The coated substrates were dried (at 80° C. for 5 minutes) in an oven to obtain formed bodies.

The used substrates are shown below.
ZEONOR Film ZF-16 (manufactured by ZEON Corporation, cycloolefin polymer (COP), 188 μm)
ZEONEX790R (manufactured by ZEON Corporation, cycloolefin polymer (COP), 2 mm)
APEL 6015T (manufactured by Mitsui Chemicals, Inc., cycloolefin copolymer (COC), 2 mm)
Optica Film 6013T (manufactured by Mitsui Chemicals, Inc., COC film, 100 μm)
TOPAS 6015S (manufactured by POLYPLASTICS CO., LTD., COC, 1 mm)
TPX RT18 (manufactured by Mitsui Chemicals, Inc., a methyl pentene copolymer, 2 mm)
MX0200 (manufactured by Mitsui Chemicals, Inc., a methyl pentene copolymer, 2 mm)
Polyethylene plate (Wako, 1 mm)
Polypropylene plate (Wako, 1 mm)

Example 2

(1) Synthesis of N,N-Di-p-tolylacrylamide

[Formula 2]

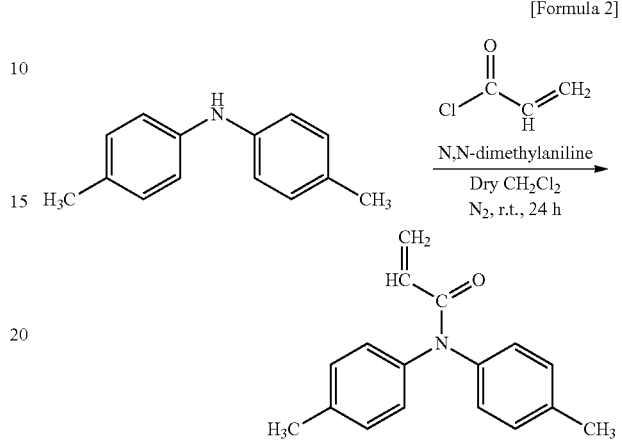

Di-p-tolylamine (5.00 g, 25.3 mmol), N,N-dimethylaniline (3.69 g, 30.4 mmol), and 50 mL of super-dehydrated dichloromethane were added to a 100 mL four-necked flask replaced with nitrogen. The reaction solution was cooled to 10° C. or less in an ice bath, acrylic acid chloride (2.75 g, 30.4 mmol) was slowly dropped, and the mixture was stirred for 30 minutes. Then, the temperature of the reaction liquid was raised to room temperature, and the reaction was performed for 24 hours. After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The crude product was purified by column chromatography (ethyl acetate/hexane=3/7, silica gel) to obtain N,N-di-p-tolylacrylamide (2.87 g, yield 45%). The result of mass spectrometry analysis is shown below.

High Resolution ESI-TOF-MS m/z Calcd. for $[C_{17}H_{17}N_1O_1([M+Na]^+)]$: 274.1202 found 274.1221.

(2) Preparation of Poly(N,N-di-p-tolylacrylamide)

The polymer was prepared by the same method as Example 1 except that 1.00 g of N,N-di-p-tolylacrylamide and 8.3 mg of AIBN were used. By GPC, the number average molecular weight ($M_n$) of the polymer was 24,900, and the molecular weight distribution (PDI) was 1.95.

(3) Preparation of Coating Agent

Then, 0.1 g of poly(N,N-di-p-tolylacrylamide) was dissolved in 9.9 g of cyclohexanone by heating to obtain a coating agent (B-1) having a solid concentration of 1 wt %.

(4) Formation of Coating Film

Except that (B-1) was used for the coating agent, the same operation as Example 1 was performed.

Example 3

(1) Synthesis of N,N-Di-4-methoxyphenylacrylamide

[Formula 3]

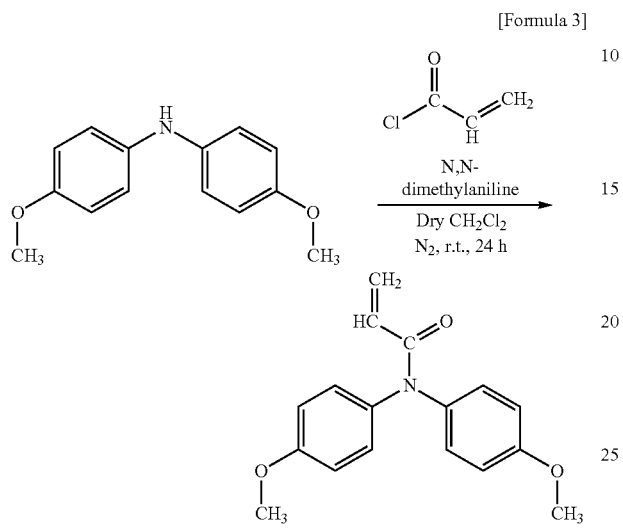

Bis(4-methoxyphenyl)amine (5.00 g, 21.8 mmol), N,N-dimethylaniline (3.17 g, 26.2 mmol), and 50 mL of super-dehydrated dichloromethane were added to a 100 mL four-necked flask replaced with nitrogen. The reaction solution was cooled to 10° C. or less in an ice bath, acrylic acid chloride (2.37 g, 26.2 mmol) was slowly dropped, and the mixture was stirred for 30 minutes. Then, the temperature of the reaction liquid was raised to room temperature, and the reaction was performed for 24 hours. After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The crude product was purified by column chromatography (ethyl acetate/hexane=3/7, silica gel) to obtain N,N-di-4-methoxyphenylacrylamide (3.83 g, yield 62%). The result of mass spectrometry analysis is shown below.

High Resolution ESI-TOF-MS m/z Calcd. for $[C_{17}H_{17}N_1O_3([M+Na]^+)]$: 306.1101 found 306.1109.

(2) Preparation of Poly(N,N-Di-4-methoxyphenylacrylamide)

The polymer was prepared by the same method as Example 1 except that 1.00 g of N,N-di-4-methoxyphenylacrylamide and 7.16 mg of AIBN were used. By GPC, the number average molecular weight ($M_n$) of the polymer was 28,900, and the molecular weight distribution (PDI) was 1.73.

(3) Preparation of Coating Agent

Then, 0.1 g of poly(N,N-di-4-methoxyphenylacrylamide) was dissolved in 9.9 g of cyclohexanone by heating to obtain a coating agent (C-1) having a solid concentration of 1 wt %.

(4) Formation of Coating Film

Except that (C-1) was used for the coating agent, the same operation as Example 1 was performed.

Example 4

(1) Synthesis of N-Acryloyl Dihydroacridine

[Formula 4]

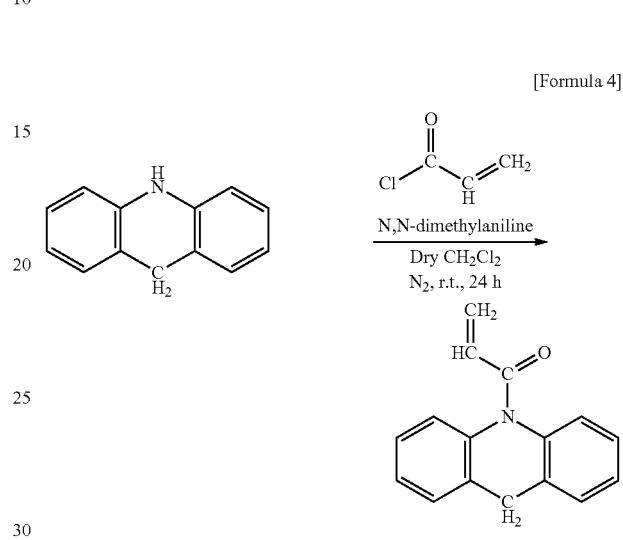

9,10-dihydroacridine (5.00 g, 27.6 mmol), N,N-dimethylaniline (6.69 g, 55.2 mmol), and 50 mL of super-dehydrated dichloromethane were added to a 100 mL four-necked flask replaced with nitrogen. The reaction solution was cooled to 10° C. or less in an ice bath, acrylic acid chloride (3.75 g, 41.4 mmol) was slowly dropped, and the mixture was stirred for 30 minutes. Then, the temperature of the reaction liquid was raised to room temperature, and the reaction was performed for 24 hours. After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The crude product was purified by column chromatography (ethyl acetate/hexane=1/9) to obtain N-acryloyl dihydroacridine (3.05 g, yield 47%). The result of mass spectrometry analysis is shown below.

High Resolution ESI-TOF-MS m/z Calcd. for $[C_{16}H_{13}N_1O_1([M+Na]^+)]$: 258.0889 found 258.0871.

(2) Preparation of Poly(N-Acryloyl Dihydroacridine)

The polymer was prepared by the same method as Example 1 except that 1.00 g of N-acryloyl dihydroacridine and 9.06 mg of AIBN were used. By GPC, the number average molecular weight ($M_n$) of the polymer was 20,000, and the molecular weight distribution (PDI) was 1.75.

(3) Preparation of Coating Agent

Then, 0.1 g of poly(N-acryloyl dihydroacridine) was dissolved in 9.9 g of cyclohexanone by heating to obtain a coating agent (D-1) having a solid concentration of 1 wt %.

(4) Formation of Coating Film

Except that (D-1) was used for the coating agent, the same operation as Example 1 was performed.

Example 5

(1) Synthesis of N-Acryloyliminodibenzyl

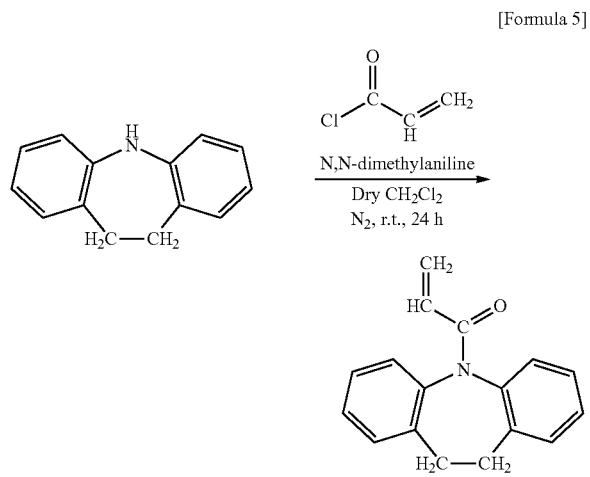

[Formula 5]

Iminodibenzyl (5.00 g, 25.6 mmol), N,N-dimethylaniline (3.72 g, 30.7 mmol), and 50 mL of super-dehydrated dichloromethane were added to a 100 mL four-necked flask replaced with nitrogen. The reaction solution was cooled to 10° C. or less in an ice bath, acrylic acid chloride (2.78 g, 30.7 mmol) was slowly dropped, and the mixture was stirred for 30 minutes. Then, the temperature of the reaction liquid was raised to room temperature, and the reaction was performed for 24 hours.

After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The crude product was purified by column chromatography (ethyl acetate/hexane=3/7) to obtain N-acryloyliminodibenzyl (3.70 g, yield 58%). The result of mass spectrometry analysis is shown below.

High Resolution ESI-TOF-MS m/z Calcd. for $[C_{17}H_{15}N_1O_1([M+Na]^+)]$: 272.1046 found 272.1065.

(2) Preparation of Poly(N-Acryloyliminodibenzyl)

The polymer was made by the same method as Example 1 except that 1.00 g of N-acryloyliminodibenzyl and 6.59 mg of AIBN were used. By GPC, the number average molecular weight ($M_n$) of the polymer was 20,000, and the molecular weight distribution (PDI) was 1.75.

(3) Preparation of Coating Agent

Then, 0.1 g of poly(N-acryloyliminodibenzyl) was dissolved in 9.9 g of cyclohexanone by heating to obtain a coating agent (E-1) having a solid concentration of 1 wt %.

(4) Formation of Coating Film

Except that (E-1) was used for the coating agent, the same operation as Example 1 was performed.

Example 6

(1) Synthesis of N-Acryloylphenoxazine

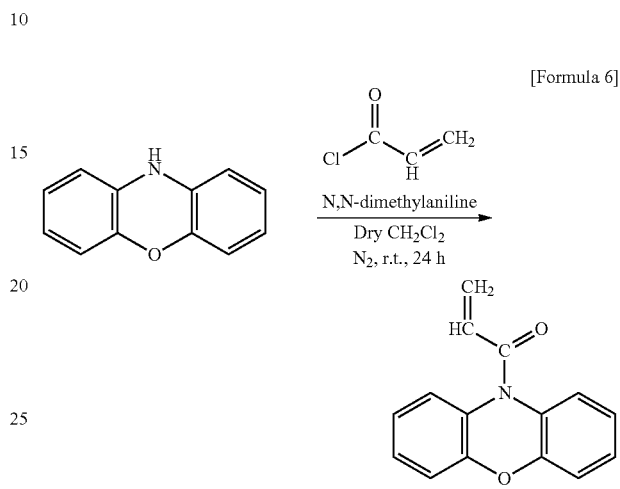

[Formula 6]

Phenoxazine (5.00 g, 27.3 mmol), N,N-dimethylaniline (6.61 g, 54.6 mmol), and 50 mL of super-dehydrated dichloromethane were added to a 100 mL four-necked flask replaced with nitrogen. The reaction solution was cooled to 10° C. or less in an ice bath, acrylic acid chloride (3.71 g, 40.9 mmol) was slowly dropped, and the mixture was stirred for 30 minutes. Then, the temperature of the reaction liquid was raised to room temperature, and the reaction was performed for 24 hours. After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The crude product was purified by column chromatography (ethyl acetate/hexane=3/7) to obtain 3.89 g (yield 60%) of N-acryloylphenoxazine. The result of mass spectrometry analysis is shown below.

High Resolution ESI-TOF-MS m/z Calcd. for $[C_{15}H_{11}N_1O_2([M+Na]^+)]$: 260.0682 found 260.0691.

(2) Preparation of Poly(N-Acryloylphenoxazine)

The polymer was prepared by the same method as Example 1 except that 1.00 g of N-acryloylphenoxazine and 6.92 mg of AIBN were used. By GPC, the number average molecular weight ($M_n$) of the polymer was 31,200, and the molecular weight distribution (PDI) was 1.83.

(3) Preparation of Coating Agent

Then, 0.1 g of poly(N-acryloylphenoxazine) was dissolved in 9.9 g of cyclohexanone by heating to obtain a coating agent (F-1) having a solid concentration of 1 wt %.

(4) Formation of Coating Film

Except that (F-1) was used for the coating agent, the same operation as Example 1 was performed.

Example 7

(1) Synthesis of N-Acryloylphenothiazine

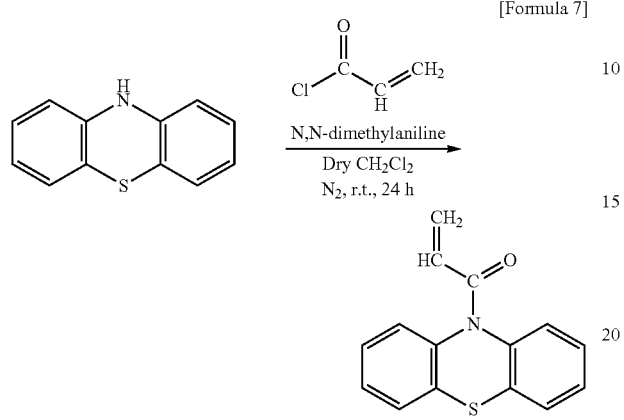

[Formula 7]

Phenothiazine (5.00 g, 25.1 mmol), N,N-dimethylaniline (6.08 g, 50.2 mmol), and 50 mL of super-dehydrated dichloromethane were added to a 100 mL four-necked flask replaced with nitrogen. The reaction solution was cooled to 10° C. or less in an ice bath, acrylic acid chloride (3.41 g, 37.6 mmol) was slowly dropped, and the mixture was stirred for 30 minutes. Then, the temperature of the reaction liquid was raised to room temperature, and the reaction was performed for 24 hours. After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The crude product was purified by column chromatography (ethyl acetate/hexane=3/7) to obtain N-acryloylphenothiazine (3.81 g, yield 60%). The result of mass spectrometry analysis is shown below.

High Resolution ESI-TOF-MS m/z Calcd. for $[C_{15}H_{11}N_1O_1S_1 ([M+Na]^+)]$: 276.0454 found 276.0478.

(2) Preparation of Poly(N-Acryloylphenothiazine)

The polymer was prepared by the same method as Example 1 except that 1.00 g of N-acryloylphenothiazine and 6.92 mg of AIBN were used. By GPC, the number average molecular weight ($M_n$) of the polymer was 31,200, and the molecular weight distribution (PDI) was 1.61.

(3) Preparation of Coating Agent

Then, 0.1 g of poly(N-acryloylphenothiazine) was dissolved in 9.9 g of cyclohexanone by heating to obtain a coating agent (G-1) having a solid concentration of 1 wt %.

(4) Formation of Coating Film

Except that (G-1) was used for the coating agent, the same operation as Example 1 was performed.

Example 8

(1) Synthesis of N,N-Di-2-naphthyl-acrylamide

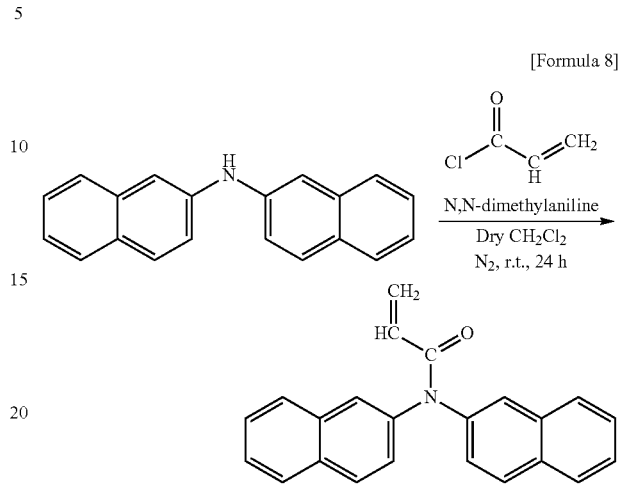

[Formula 8]

Di-2-naphthylamine (5.00 g, 18.6 mmol), N,N-dimethylaniline (4.50 g, 37.1 mmol), and 50 mL of super-dehydrated dichloromethane were added to a 100 mL four-necked flask replaced with nitrogen. The reaction solution was cooled to 10° C. or less in an ice bath, acrylic acid chloride (2.52 g, 27.8 mmol) was slowly dropped, and the mixture was stirred for 30 minutes. Then, the temperature of the reaction liquid was raised to room temperature, and the reaction was performed for 24 hours. After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The crude product was purified by column chromatography (ethyl acetate/hexane=1/10) to obtain N,N-di-2-naphthyl-acrylamide (2.94 g, yield 49%). The result of mass spectrometry analysis is shown below.

High Resolution ESI-TOF-MS m/z Calcd. for $[C_{23}H_{17}N_1O_1([M+Na]^+)]$: 346.1202 found 346.1200.

(2) Preparation of Poly(N,N-Di-2-naphthyl-acrylamide)

The polymer was prepared by the same method as Example 1 except that 1.00 g of N,N-di-2-naphthyl-acrylamide and 5.08 mg of AIBN were used. By GPC, the number average molecular weight ($M_n$) of the polymer was 29,100, and the molecular weight distribution (PDI) was 1.39.

(3) Preparation of Coating Agent

Then, 0.1 g of poly(N,N-di-2-naphthyl-acrylamide) was dissolved in 9.9 g of cyclohexanone by heating to obtain a coating agent (H-1) having a solid concentration of 1 wt %.

(4) Formation of Coating Film

Except that (H-1) was used for the coating agent, the same operation as Example 1 was performed.

Example 9

(1) Making of [N,N-Diphenylacrylamide]/[N,N-Di-p-tolylacrylamide] Copolymer

The polymer was prepared by the same method as Example 1 except that N,N-diphenylacrylamide (5.00 g, 22.4 mmol), N,N-di-p-tolylacrylamide (6.35 g, 22.4 mmol), and AIBN (36.8 mg, 0.22 mmol) were used. By GPC, the number average molecular weight ($M_n$) of the copolymer was 23,100, and the molecular weight distribution (PDI) was 1.91.

(2) Preparation of Coating Agent

Then, 0.1 g of the [N,N-diphenylacrylamide]/[N,N-di-p-tolylacrylamide] copolymer was dissolved in 9.9 g of cyclohexanone by heating to obtain a coating agent (I-1) having a solid concentration of 1 wt %.

(3) Formation of Coating Film

Except that (I-1) was used for the coating agent, the same operation as Example 1 was performed.

Example 10

(1) Preparation of [N,N-Diphenylacrylamide]/[N,N-Di-2-naphthyl-acrylamide] Copolymer The polymer was prepared by the same method as Example 1 except that N,N-diphenylacrylamide (5.00 g, 22.4 mmol), N,N-di-2-naphthyl-acrylamide (7.23 g, 22.4 mmol), and AIBN (36.8 mg, 0.22 mmol) were used. By GPC, the number average molecular weight ($M_n$) of the copolymer was 28,600, and the molecular weight distribution (PDI) was 1.87.

(2) Preparation of Coating Agent

Then, 0.1 g of the [N,N-diphenylacrylamide]/[N,N-di-2-naphthyl-acrylamide] copolymer was dissolved in 9.9 g of cyclohexanone by heating to obtain a coating agent (J-1) having a solid concentration of 1 wt %.

(3) Formation of Coating Film

Except that (J-1) was used for the coating agent, the same operation as Example 1 was performed.

Example 11

(1) Preparation of [N,N-Diphenylacrylamide]/[N-Acryloyliminodibenzyl] Copolymer

The polymer was prepared by the same method as Example 1 except that N,N-diphenylacrylamide (5.00 g, 22.4 mmol), N-acryloyliminodibenzyl (5.58 g, 22.4 mmol), and AIBN (36.8 mg, 0.22 mmol) were used. By GPC, the number average molecular weight (Ma) of the copolymer was 27,300, and the molecular weight distribution (PDI) was 2.33.

(2) Preparation of Coating Agent

Then, 0.1 g of the [N,N-diphenylacrylamide]/[N-acryloyliminodibenzyl] copolymer was dissolved in 9.9 g of cyclohexanone by heating to obtain a coating agent (K-1) having a solid concentration of 1 wt %.

(3) Formation of Coating Film

Except that (K-1) was used for the coating agent, the same operation as Example 1 was performed.

Example 12

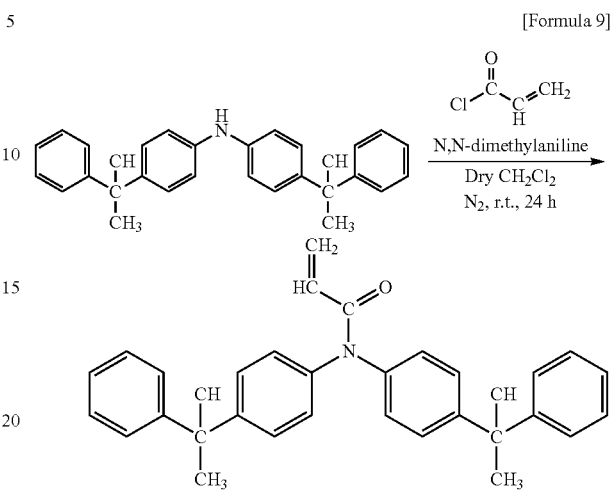

[Formula 9]

(1) Synthesis of N,N-[4,4'-bis($\alpha,\alpha$-dimethylbenzyl)diphenyl]acrylamide First, 4,4'-bis($\alpha,\alpha$-dimethylbenzyl)diphenylamine (25.00 g, 61.6 mmol), N,N-dimethylaniline (14.9 g, 123 mmol), and 200 mL of super-dehydrated dichloromethane were added to a 100 mL four-necked flask replaced with nitrogen. The reaction solution was cooled to 10° C. or less in an ice bath, acrylic acid chloride (6.69 g, 74.0 mmol) was slowly dropped, and the mixture was stirred for 30 minutes. Then, the temperature of the reaction liquid was raised to room temperature, and the reaction was performed for 24 hours. After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The obtained crude product was recrystallized with ethyl acetate/hexane to obtain N,N-[4,4'-bis($\alpha,\alpha$-dimethylbenzyl)diphenyl]acrylamide (22.95 g, yield 81%). The result of mass spectrometry analysis is shown below.

High Resolution ESI-TOF-MS m/z Calcd. for [$C_{33}H_{33}NO$ ([M+Na]$^+$)]: 482.2454 found 482.2411.

(2) Preparation of Poly{N,N-[4,4'-Bis($\alpha,\alpha$-dimethylbenzyl)diphenyl]acrylamide}

The polymer was prepared by the same method as Example 1 except that 1.00 g of N,N-[4,4'-bis($\alpha,\alpha$-dimethylbenzyl)diphenyl]acrylamide and 9.20 mg of AIBN were used. By GPC, the number average molecular weight ($M_n$) of the polymer was 29,900, and the molecular weight distribution (PDI) was 1.88.

(3) Preparation of Coating Agent

Then, 0.1 g of poly{N,N-[4,4'-bis($\alpha,\alpha$-dimethylbenzyl)diphenyl]acrylamide} was dissolved in 9.9 g of cyclohexanone by heating to obtain a coating agent (L-1) having a solid concentration of 1 wt %.

(4) Formation of Coating Film

Except that (L-1) was used for the coating agent, the same operation as Example 1 was performed.

Example 13

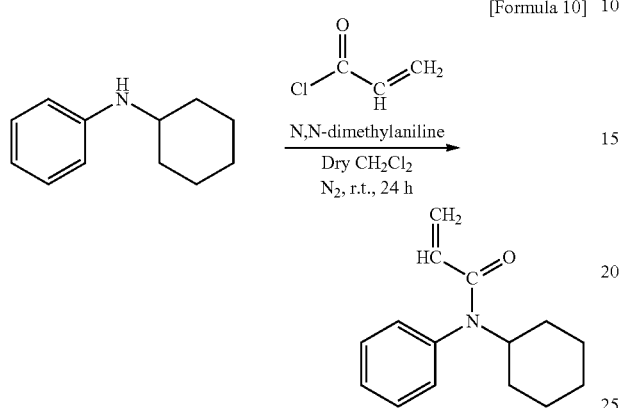

[Formula 10]

(1) Synthesis of N,N-Cyclohexylphenylacrylamide

N-Cyclohexylaniline (10.0 g, 57.1 mmol), N,N-dimethylaniline (8.30 g, 68.5 mmol), and 50 mL of super-dehydrated dichloromethane were added to a 100 mL four-necked flask replaced with nitrogen. The reaction solution was cooled to 10° C. or less in an ice bath, acrylic acid chloride (6.20 g, 68.5 mmol) was slowly dropped, and the mixture was stirred for 30 minutes. Then, the temperature of the reaction liquid was raised to room temperature, and the reaction was performed for 24 hours.

After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The obtained crude product was recrystallized with methanol/water to obtain N,N-cyclohexylphenylacrylamide (9.68 g, yield 74%). The result of mass spectrometry analysis is shown below.

High Resolution ESI-TOF-MS m/z Calcd. for $[C_{15}H_{19}NO([M+Na]^+)]$: 252.1359 found 252.1358.

(2) Preparation of Poly(N,N-Cyclohexylphenylacrylamide)

The polymer was prepared by the same method as Example 1 except that 1.00 g of N,N-cyclohexylphenylacrylamide and 2.90 mg of AIBN were used. By GPC, the number average molecular weight ($M_n$) of the polymer was 26,700, and the molecular weight distribution (PDI) was 1.79.

(3) Preparation of Coating Agent

Then, 0.1 g of poly(N,N-cyclohexylphenylacrylamide) was dissolved in 9.9 g of cyclohexanone by heating to obtain a coating agent (M-1) having a solid concentration of 1 wt %.

(4) Formation of Coating Film

Except that (M-1) was used for the coating agent, the same operation as Example 1 was performed.

Example 14

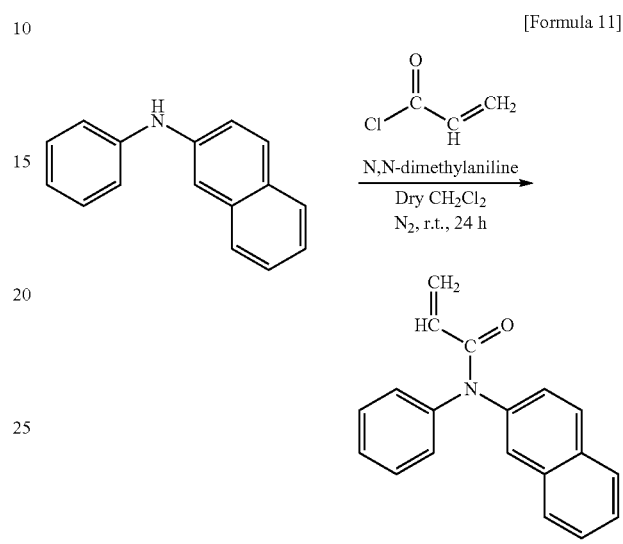

[Formula 11]

(1) Synthesis of N,N-Phenyl-2-naphthylacrylamide

N-Phenyl-2-naphthylamine (10.0 g, 50.2 mmol), N,N-dimethylaniline (12.2 g, 100 mmol), and 100 mL of super-dehydrated dichloromethane were added to a 100 mL four-necked flask replaced with nitrogen. The reaction solution was cooled to 10° C. or less in an ice bath, acrylic acid chloride (5.45 g, 60.2 mmol) was slowly dropped, and the mixture was stirred for 30 minutes. Then, the temperature of the reaction liquid was increased to room temperature, and the reaction was performed for 24 hours. After the completion of the reaction, the reaction solution was washed with 1 N aqueous hydrochloric acid solution, saturated aqueous sodium bicarbonate solution, and salt solution. The organic layer was dried over magnesium sulfate and then the filtrate was distilled off by an evaporator. The obtained crude product was purified by column chromatography (toluene/hexane=5/5) to obtain N,N-phenyl-2-naphthylacrylamide (10.45 g, 76%). The result of mass spectrometry analysis is shown below.

High Resolution ESI-TOF-MS m/z Calcd. for $[C_{15}H_{15}NO([M+Na]^+)]$: 296.1046 found 296.1067.

(2) Preparation of Poly(N,N-Phenyl-2-naphthylacrylamide)

The polymer was prepared by the same method as Example 1 except that 1.00 g of N,N-phenyl-2-naphthylacrylamide and 2.00 mg of AIBN were used. From GPC, the number average molecular weight ($M_n$) of the polymer was 31,100, and the molecular weight distribution (PDI) was 2.01.

(3) Preparation of Coating Agent

Then, 0.1 g of poly(N,N-phenyl-2-naphthylacrylamide) was dissolved in 9.9 g of cyclohexanone by heating to obtain a coating agent (N-1) having a solid concentration of 1 wt %.

(4) Formation of Coating Film

Except that (N-1) was used for the coating agent, the same operation as Example 1 was performed.

Example 15

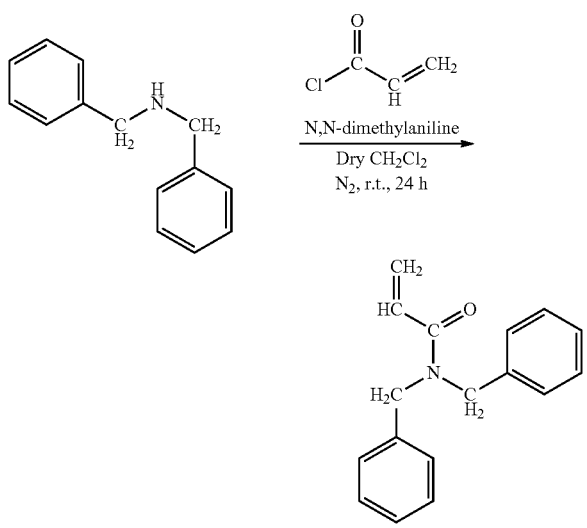

[Formula 12]

(1) Synthesis of N,N-Dibenzylacrylamide

Dibenzylamine (5.00 g, 25.3 mmol), N,N-dimethylaniline (3.85 g, 31.8 mmol), and 100 mL of super-dehydrated dichloromethane were added to a 100 mL four-necked flask replaced with nitrogen. The reaction solution was cooled to 10° C. or less in an ice bath, acrylic acid chloride (2.75 g, 30.4 mmol) was slowly dropped, and the mixture was stirred for 30 minutes. Then, the temperature of the reaction liquid was raised to room temperature, and the reaction was performed for 24 hours. After the completion of the reaction, the reaction solution was washed with 1 N aqueous hydrochloric acid solution, saturated aqueous sodium bicarbonate solution, and brine. The organic layer was dried over magnesium sulfate and then the filtrate was distilled off by an evaporator. The obtained crude product was purified by column chromatography (toluene/ethyl acetate=10/1) to obtain N,N-dibenzylacrylamide (5.15 g, yield 81%). The result of mass spectrometry analysis is shown below. High Resolution ESI-TOF-MS m/z Calcd. for $[C_{33}H_{33}NO([M+Na]^+)]$: 274.1202 found 274.1162.

(2) Preparation of Poly(N,N-dibenzylacrylamide)

The polymer was made by the same method as Example 1 except that 5.00 g of N,N-dibenzylacrylamide and 9.20 mg of AIBN were used. By GPC, the number average molecular weight ($M_n$) of the polymer was 24,700, and the molecular weight distribution (PDI) was 1.59.

(3) Preparation of Coating Agent

Then, 0.1 g of poly(N,N-dibenzylacrylamide) was dissolved in 9.9 g of cyclohexanone by heating to obtain a coating agent (O-1) having a solid concentration of 1 wt %.

(4) Formation of Coating Film

Except that (O-1) was used for the coating agent, the same operation as Example 1 was performed.

(Peeling Test)

To show that the coating agents of the present invention have excellent adhesiveness to substrates, the cross-cut peeling test of old JIS K5400 was performed on each of the formed bodies obtained in the above Examples 1 to 15.

The test results are shown in the following table.

In the table, the denominator of a fraction represents the number of all the squares (100 pieces), and the numerator represents the number of squares that are not peeled. 100/100 shows that none of the 100 squares are peeled.

TABLE 1

| SUBSTRATE | A-1 | B-1 | C-1 | D-1 | E-1 | F-1 | G-1 | H-1 | I-1 | J-1 | K-1 | L-1 | M-1 | N-1 | O-1 |
|---|---|---|---|---|---|---|---|---|---|---|---|---|---|---|---|
| ZEONOR Film ZF-16 | 100/100 | 100/100 | 100/100 | 100/100 | 100/100 | 100/100 | 100/100 | 100/100 | 100/100 | 100/100 | 100/100 | 100/100 | 100/100 | 100/100 | 56/100 |
| ZEONEX790R | 100/100 | 100/100 | 100/100 | 100/100 | 100/100 | 100/100 | 100/100 | 100/100 | 100/100 | 100/100 | 100/100 | 100/100 | 100/100 | 100/100 | 71/100 |
| APEL6015T | 100/100 | 100/100 | 100/100 | 100/100 | 100/100 | 100/100 | 100/100 | 100/100 | 100/100 | 100/100 | 100/100 | 100/100 | 100/100 | 100/100 | 100/100 |
| OPTICA FILM 6013T | 100/100 | 100/100 | 100/100 | 100/100 | 100/100 | 100/100 | 100/100 | 100/100 | 100/100 | 100/100 | 100/100 | 100/100 | 100/100 | 100/100 | 100/100 |
| TOPAS 6015S | 100/100 | 100/100 | 100/100 | 100/100 | 100/100 | 100/100 | 100/100 | 100/100 | 100/100 | 100/100 | 100/100 | 100/100 | 100/100 | 100/100 | 100/100 |
| TPX RT18 | 100/100 | 100/100 | 100/100 | 100/100 | 100/100 | 100/100 | 100/100 | 100/100 | 100/100 | 100/100 | 100/100 | 100/100 | 100/100 | 100/100 | 2/100 |
| TPX MX0200 | 100/100 | 100/100 | 100/100 | 100/100 | 100/100 | 100/100 | 100/100 | 100/100 | 100/100 | 100/100 | 100/100 | 100/100 | 100/100 | 100/100 | 11/100 |
| PE | 100/100 | 100/100 | 100/100 | 100/100 | 100/100 | 100/100 | 100/100 | 100/100 | 100/100 | 100/100 | 100/100 | 100/100 | 100/100 | 100/100 | 49/100 |
| PP | 100/100 | 100/100 | 100/100 | 100/100 | 100/100 | 100/100 | 100/100 | 100/100 | 100/100 | 100/100 | 100/100 | 100/100 | 100/100 | 100/100 | 19/100 |

Example 16

The polymerization reaction was performed with reference to Macromol. Rapid. Commun. 2005, 26, 1499-1503. 10.0 g (45 mmol) of N,N-diphenylacrylamide and 100 mL of THF were added to a 300 ml four-necked flask, and the mixture was stirred for 15 minutes. It is checked that the mixture was dissolved homogeneously, and the reaction mixture was subsequently cooled to 0° C. or less using an ice bath. Then, 0.23 mL (0.22 mmol) of 23% TIBAL in toluene was dropped. After the reaction solution was stirred for 30 minutes, it was deactivated using 2 M mixed solution of HCl/MeOH, and then reprecipitation was performed using excess methanol. White powder obtained by filtration was dried under reduced pressure—at 120° C. for 6 hours. When the obtained poly(N,N-diphenylacrylamide) was analyzed by GPC, the number average molecular weight ($M_n$) was 138,100, and the molecular weight dispersion (PDI) was 1.29 in terms of a standard poly(methyl methacrylate) equivalent number average molecular weight.

The obtained poly(N,N-diphenylacrylamide) was dissolved in cyclohexanone at 1 wt %. The coating agent was applied to a ZEONOR Film ZF-16, ZEONEX790R, and APL6015T by the bar coating method and dried by heat at 100° C. for 3 minutes to make laminated samples. When the adhesiveness of the obtained samples was evaluated by the JIS K5400 cross-cut tape peeling test, all samples showed the result of 100/100.

From the test results, it is shown that the adhesive composition of the present invention has excellent adhesiveness especially to a cycloolefin resin substrate.

(Test as Adhesive)
(1) Preparation of Adhesive 0.2 g of poly(N,N-diphenylacrylamide) obtained in Example 1 was dissolved in 0.8 g of tetrahydrofuran to obtain an adhesive (L-1) having a solid concentration of 10 wt %.

(2) Preparation of Adhesiveness Test Sample

Two PE boards of a size of 25×50×1.0 mm were adhered together in an area of 25×25 mm using 0.1 g of the adhesive (L-1). The adhered part was fixed with a clip and dried by heat at 50° C. for 30 minutes to obtain an adhesiveness test sample.

(3) Tensile Shear Peeling Test

A tensile shear peeling test was performed as an adhesiveness test. A SIMAZU AGS-J universal tensile tester comprising a load cell of 1 kN was used for the test. The device was equipped with the adhesiveness test sample obtained in (2), and the test was performed at a speed of 1 mm/min. The test was performed at room temperature. The obtained adhesive strength was 0.61 MPa.

From the test result, it is found that the adhesive composition of the present invention has excellent adhesiveness.

The invention claimed is:

1. A compound represented by Formula (I):

Y—N(Ar)(R)  Formula (I)

wherein:
  each of Ar and R represents, respectively, a phenyl group which is substituted by either a benzyl group or a α,α-dimethylbenzyl group, and
  Y represents an acryloyl group or a methacryloyl group.

* * * * *